United States Patent [19]

Darsow

[11] Patent Number: 5,641,872
[45] Date of Patent: Jun. 24, 1997

[54] PROCESS FOR THE HYDROGENATION OF SUGARS

[75] Inventor: Gerhard Darsow, Krefeld, Germany

[73] Assignee: Bayer Aktiengesellschaft, Leverkusen, Germany

[21] Appl. No.: 431,603

[22] Filed: May 1, 1995

[30] Foreign Application Priority Data

May 10, 1994 [DE] Germany ................... 44 16 408

[51] Int. Cl.$^6$ .................... C07C 29/132; C07C 31/18
[52] U.S. Cl. .................... 536/18.5; 536/1.11; 536/4.1; 536/124; 568/863
[58] Field of Search .................... 536/1.1, 4.1, 18.5, 536/123.13, 124; 423/53, 61; 568/861, 862, 863

[56] References Cited

U.S. PATENT DOCUMENTS

| | | | |
|---|---|---|---|
| 3,691,100 | 9/1972 | Wright | 252/458 |
| 3,741,776 | 6/1973 | Mitsuhashi et al. | 99/141 |
| 3,865,957 | 2/1975 | Schieweck et al. | 426/213 |
| 4,117,173 | 9/1978 | Schiweck et al. | 426/548 |
| 4,322,569 | 3/1982 | Chao et al. | 568/863 |
| 4,433,184 | 2/1984 | Huibers et al. | 568/863 |
| 4,608,446 | 8/1986 | Mohring et al. | 568/863 |
| 4,684,720 | 8/1987 | Darsow et al. | 536/124 |
| 5,162,517 | 11/1992 | Darsow | 536/124 |

FOREIGN PATENT DOCUMENTS

| | | |
|---|---|---|
| 0039981 | 8/1983 | European Pat. Off. . |
| 04103546 | 4/1992 | Japan . |

OTHER PUBLICATIONS

Ivchenko et al., *Uzb. Khim. Zh.*, vol. 3:66–8, (1990). Abstract Only.

Kirgizbaev et al., *Uzb. Khim. Zh.*, vol. 5:59–62, (1988). Abstract Only.

Pintauro et al. AIChE Symp. Ser. 83 (254, Electrochem. Eng. Appl.) pp. 34–39, (1987). Abstract Only.

Derwent Database, Derwent week 7602, a.n. 76–03375, abstract of SU 453 187 (1976).

Derwent Database, Derwent Week 9241, a.n. 92–334368, abstract of HU 60,230 (1991).

*Primary Examiner*—John Kight
*Assistant Examiner*—Howard C. Lee
*Attorney, Agent, or Firm*—Sprung Horn Kramer & Woods

[57] ABSTRACT

The sugar alcohols mentioned as title compounds can be prepared from the corresponding sugars by catalytic hydrogenation in aqueous solution with hydrogen, the hydrogenation being carded out continuously at a hydrogen pressure of 100 to 400 bar and a reaction temperature of 40° to 80° C. on support-free shaped bodies which are arranged in a fixed bed and are composed of pressed powders of alloys of the elements of the iron sub group of sub group VIII of the Periodic Table of the Elements containing elements of sub group VI. The shaped bodies have a compressive strength of 20 to 250 N and an internal surface area of 10 to 80 m$^2$/g.

13 Claims, No Drawings

PROCESS FOR THE HYDROGENATION OF SUGARS

The invention relates to an inexpensive process for the continuous catalytic hydrogenation of sugars such as D-xylose, α-D-glucose, 4-O-β-D-galactopyranosyl-α-D-glucopyranose or 4-O-α-D-glucopyranosyl-α-D-glucopyranose with hydrogen to give the corresponding sugar alcohols, such as xylitol, sorbitol, 4-O-β-D-galactopyranosyl-D-sorbitol or 4-O-α-D-glucopyranosyl-D-sorbitol.

The course of the reaction can be illustrated by the following reaction diagrams:

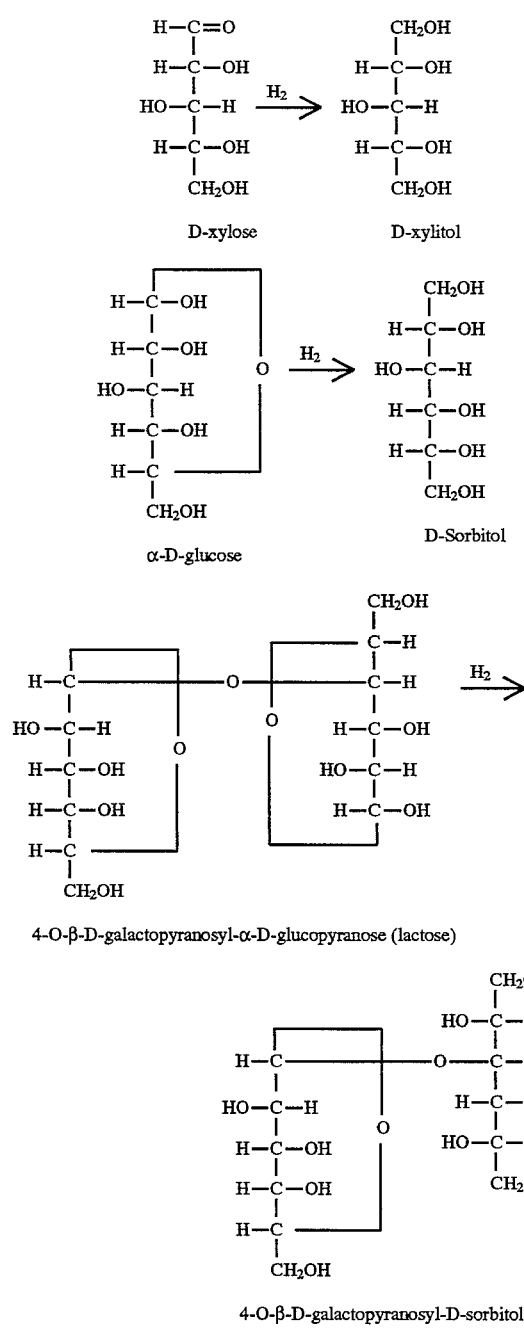

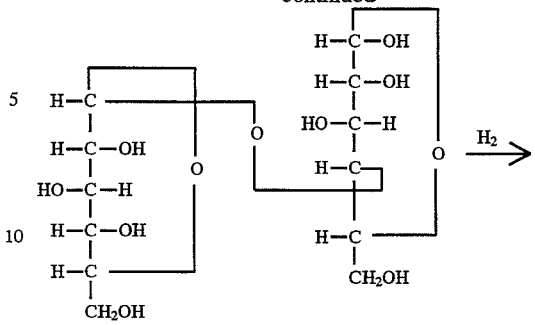

4-O-α-D-glucopyranosyl-α-D-glucopyranose (maltose)

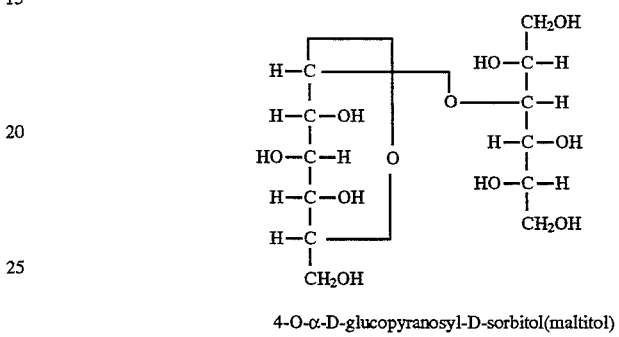

4-O-α-D-glucopyranosyl-D-sorbitol(maltitol)

For the preparation of xylitol or sorbitol, a discontinuous process is generally employed in which a pulverulent nickel catalyst is used in a suspension process.

A discontinuous process is also disclosed for the preparation of lactitol, which has not hitherto been found in nature, by EP-A 39 981 in which a pulverulent nickel catalyst is used in a suspension process.

Such a process is also proposed in US Patent Specification 3 741 776 for the preparation of maltitol.

Discontinuous processes have the disadvantage that their capacity, relative to the reaction volume, is very small and there is thus a requirement for large reaction apparatuses and storage tanks. The energy consumption is uneconomical and the labor requirement is relatively high.

Continuous powder catalyst processes which employ a plurality of hydrogenation reactors connected in a cascade avoid some of the said disadvantages. However, the method remains a complex one of specifically activating the pulverulent catalyst, pumping it in circulation and quantitatively filtering it off from the reaction product. The catalyst slurry pumps are subject to a high mechanical loading. The quantitative removal of the pulverulent catalyst is complex (coarse and fine filtration apparatuses in alternate configuration). In addition, there is the high risk of the catalyst losing its activity relatively rapidly as a result of the additional operations (high catalyst consumption). It is therefore desirable to allow the reaction to proceed over fixed catalysts which are to have a high specific activity which should also not decrease over a relatively long period of one to several years, since frequent changes of catalyst are complex even in the case of fixed-bed reactions.

It is also conventional in the case of fixed catalysts to connect a plurality of reactors one after the other, which results in a plurality of series-connected reaction zones (German Offenlegungsschrift A 3 214 432).

Nickel catalysts on an oxidic support material ($SiO_2$/$Al_2O_3$) having extremely large active surface areas of 140 to 180 $m^2$/g have been predominantly used hitherto, so that the catalysts are active in such a manner that they have to be stabilized by additional chemical treatment methods, for example by oxygen gas treatment for the formation of monomolecular oxygen layers on the catalyst surface (German Offenlegungsschrift 3 110 493). However, the deactivating stabilization of the catalyst then makes necessary reaction temperatures in the hydrogenation which are so high (130° to 180° C.) that uncontrollable side reactions become possible, such as discoloration as a result of caramelization and hydrogenating cracking (hydrogenolysis) of the sugar alcohols until methanol and even methane are formed. Moreover, in this type of reaction, relatively large portions of heavy metals continuously pass into solution in ionic or colloidal form which on the one hand makes necessary subsequent activated charcoal treatment of the hydrogenated product and on the other hand deionization by ion exchangers.

Since the known hydrogenation processes employ sugar solutions adjusted to pHs of 7 to 13, alkali metals or alkaline earth metals must be added to the starting solutions and must be likewise laboriously removed again from the end product (German Offenlegungsschrift 3 110 493; German Offenlegungsschrift 3 214 432).

Furthermore it is to be expected that under the hydrogenating conditions a marked epimerization occurs so that, for example, from D-xylose, apart from xylitol, lyxitol (or arabitol and ribitol) are also obtained; from α-D-glucose, in addition to sorbitol, mannitol would also be expected.

In addition, the effect of the splitting of the carbon chain of sugars is known in the catalytic hydrogenation by Raney nickel; German Offenlegungschrift 2 756 270 describes the effect on a sugar mixture, as originates from the self-condensation of formaldehyde, a marked shift being observed, in the context of the illustrative examples given there, from higher C chain numbers to lower C chain numbers.

EP-A 423 525 discloses a process for the continuous hydrogenation of sugars to give the corresponding epimer-free sugar alcohols on support-free solid bodies of elements of sub group VIII of the Periodic Table of the Elements, these support-free solid bodies preferably having been produced by pressing and/or gluing together metal powder. In the course of this it was shown that the sugars are not only virtually completely reacted but only one sugar alcohol in each case is obtained, avoiding epimerization and C-chain cleavage and avoiding the formation of higher-molecular components by condensation reactions with ether formation. However, it would be desirable to reduce the high catalyst costs. Moreover, the aim is always to carry out a process at the lowest possible temperature in order to reduce the energy costs.

It has now surprisingly been found that metal powders of nickel, cobalt and iron or alloys thereof, which metal powders contain elements of sub group VI of the Periodic Table of the Elements, after being pressed to give shaped bodies not only catalyse equally well the hydrogenation of xylitol, sorbitol, lactitol and maltitol to give epimer-free sugar alcohols, but that catalysts made of these metals or metal alloys which are cheaper by 30 to 45% even have a considerably higher hydrogenation activity, so that the hydrogenation reaction can be carried out at a reaction temperature lower by up to 30° C. The powders used in this case can additionally contain certain portions (maximum permissible 10% by weight) of other non-catalytically active metals (e.g. manganese, silicon, aluminium, titanium) without the high activity being decreased.

The invention therefore relates to a process for the preparation of sugar alcohols selected from the group consisting of xylitol, sorbitol, 4-O-β-D-galactopyranosyl-D-sorbitol (lactitol), 4-O-α-D-glucopyranosyl-D-sorbitol (maltitol) by catalytic hydrogenation of the corresponding sugars D-xylose, α-D-glucose, 4-O-β-D-galactopyranosyl-α-D-glucopyranose and 4-O-α-D-glucopyranosyl-α-D-glucopyranose in aqueous solution with hydrogen at elevated pressure and elevated temperature, characterized in that the hydrogenation is carried out continuously at a hydrogen pressure of 100 to 400 bar, preferably 150 to 300 bar, and temperatures of 40° to 80° C., preferably 55° to 70° C., in the fixed-bed process in a reaction zone over support-free shaped bodies serving as hydrogenation catalysts and having a compressive strength of 20 to 250 N, preferably 110 to 220 N, and an internal surface area of 10 to 80 $m^2/g$ of (i) one or more elements of the iron sub group of sub group VIII which are additionally alloyed with (ii) elements of sub group VI having activating activity.

The compressive strength of the support-free shaped bodies can be determined in accordance with DIN 50 106.

The testing of support-free shaped bodies for the internal surface areas in accordance with the claims and thus for useability for the process according to the invention can be carried out by methods which have been described by F. M. Nelsen and F. T. Eggertsen, Analyt. Chem. 30 (1958), 1387 and S. J. Gregg and S. W. Sing, Adsorption, Surface Area and Porosity, London 1967, Chapters 2 and 8.

The iron sub group of sub group VIII of the Periodic Table of the Elements contains the elements iron, cobalt and nickel. The support-free shaped bodies to be used according to the invention contain one or more of these metals in amounts of at least 60, preferably at least 70, in particular at least 80% by weight, based on support-free shaped bodies.

Sub group VI of the Periodic Table of the Elements contains the elements chromium, molybdenum and tungsten. The support-free shaped bodies to be used according to the invention contain one or more of these metals in amounts of at least 0.1, preferably at least 0.3, in particular at least 0.5% by weight, based on support-free shaped bodies; they contain one or more of these metals in amounts of at most 20, preferably at most 10 and in particular at most 5% by weight, based on support-free shaped bodies.

The support-free shaped bodies to be used according to the invention can additionally contain—in each case based on support-free shaped bodies—up to 20, preferably up to 15, in particular up to 10% by weight of other metals; examples of such metals which do not have to be catalytically active include aluminium, silicon, titanium and manganese. According to a preferred embodiment the support-free shaped bodies, apart from components (i) and (ii) contain no more than 10% by weight of aluminium and no more than 5% by weight of other metals.

The process according to the invention permits the preparation of the sugar alcohols in a purity of over 99% in dry matter. The content of unreacted sugar reaches values of 0.2% by weight or below. Since the glycosidic ether bonds in disaccharides are treated gently, the contents of mono-sugar alcohols are 0.3% by weight or below. The commercial specifications for the sugar alcohols, for example in accordance with DAB, USP or FCC, can therefore be complied with directly without further purification operations.

The following can be used as starting compound for the process according to the invention: crystalline D-xylose, α-D-glucose, α-lactose or α-lactose monohydrate or maltose (liquid or in its 13-form also as a crystalline monohydrate). The starting material is preferably dissolved in oxygen-free deionized water. In the hydrogenation of D-xylose, α-D-glucose, α-lactose and maltose, according to a preferred embodiment, the procedure is carried out in such a way that a 15 to 45% by weight strength, preferably 35 to 40% by weight strength solution results, the pH of which is 3.5 to 10.5. The solution of the monosaccharides is preferably adjusted to a pH of 3.5 to 8, that of the disaccharides preferably to a pH of 5.5 to 10.5. For all starting materials, the particularly preferred pH range is 6 to 7.5. The sugars mentioned as starting compounds dissolved in water having a pH of 7 show a neutral or, caused by a trace formation of sugar acids, a weakly acidic reaction, but can be adjusted to the desired pH, for example, by specific addition of basic water-soluble compounds, such as alkali metal carbonates or preferably ammonia in aqueous solution, or acidic compounds, such as sugar acids, sorbic acid or citric acid.

For the process according to the invention, pure hydrogen is used which is precompressed to a pressure of 100 to 400 bar, preferably 150 to 300 bar. The hydrogenation is carried out continuously in the fixed-bed process on the support-free shaped bodies serving as hydrogenation catalysts either by allowing the solution to be hydrogenated to flow cocurrently ascending from below together with the previously added hydrogen over the catalyst mounted in a hydrogenation reactor (cocurrent process) or by conducting the solution to be hydrogenated ascending from below in the opposite direction to the hydrogen flowing in from above (counter-current process).

The hydrogenation reactor can be either a single high-pressure tube made of steel or a steel alloy which is wholly or partly filled with the support-free shaped body, where at certain tube cross-sections, the employment of the support-free shaped body on hurdles (wire baskets or the like) can also be useful, or else an enclosed high-pressure tube bundle, the individual tubes of which are wholly or partly filled with support-free shaped bodies. Furthermore, instead of a relatively large individual tubular reactor, an arrangement of a plurality of small individual reactors one after the other in a cascade can be operated.

The support-free shaped bodies can be produced by conventional methods by pressing the metal powder on tableting or pelleting machines at high pressure, where to improve the adhesive strength of the metal particles, graphite can also be used in amounts of 0.5 to 1.5%, by weight, based on the total weight of the constituents forming the catalyst, or adhesives can be used in small mounts. The support-free shaped bodies are preferably produced in an oxygen-free atmosphere in order to avoid surface oxidations. Tableted or pelletized shaped bodies having diameters from 3 to 7 mm are the most effective and the most expedient for the reaction conditions. Tableted mouldings can also be provided with an axial penetrating hole to increase the external surface area. When viewed macroscopically, such mouldings have a smooth surface.

The compressive strength of the shaped bodies is of considerable importance and according to the invention has values of 20 to 250 N, preferably 110 to 220 N. Lower, compressive strengths lead to disintegration of the shaped body or to erosive wear which would produce a metallic contamination of the reaction product. The internal surface area of the shaped bodies is further of considerable importance and according to the invention has values of 10 to 80 $m^2/g$ and is decisive for as quantitative as possible conversion of the starting materials.

The hydrogenation process is carried out at a temperature of 40° to 80° C., preferably 55° to 70° C. Lower temperatures necessitate longer residence times or dispensing with a quantitative conversion of the sugars. Higher temperatures lead to uncontrolled side reactions (caramelization, ether cleavage or hydrogenating cracking), which can lead to discolorations and the formation of further undesirable by-products.

The hourly catalyst productivity can be 25 to 100 g of the sugars mentioned as starting compounds per liter of catalyst. When the reaction conditions mentioned are complied with, unexpectedly high catalyst service lives of 18,000 hours and above may be achieved, specific catalyst consumptions of 0.1% by weight or less being attained. The technical advantages of the process according to the invention, in addition to the high yield caused by the virtually quantitative conversion and the ecological advantages resulting from the purity of the prepared product, are therefore the extremely low catalyst consumption and the low catalyst costs.

The aqueous sugar alcohol solution leaving the reactor can, after depressurization in which the excess hydrogen can be collected and reused after repeated compression and make up with further hydrogen, already be used as a sugar substitute in liquid form.

The water of this solution can be removed in various ways, for example via spray-driers, roller-driers or by freeze-drying. It has proved to be expedient to concentrate the generally glass-clear sugar alcohol solution obtained to a sugar alcohol content of about 70 to 80% by weight in a falling-film evaporator or a similarly operating apparatus and then to bring the solution to partial or complete crystallization after further evaporation in a vacuum crystallization apparatus with cooling. The crystals can be brought to a uniform grain size by a downstream grinding process and possibly screening. The product obtained is flowable.

Xylitol has a melting point of 93° to 94° C. In the case of sorbitol, depending on the crystallization conditions, various crystalline modifications can arise of which the γ form having a melting point of 101° C. is the most stable.

Depending on the crystallization conditions, lactitol can be obtained either as a dihydrate having a melting point of 76° to 78° C. or as a monohydrate having a melting point of 121° to 123° C. The solubility of the two hydrates in water is different; the monohydrate is less soluble than the dihydrate. The hydrates are non hygroscopic and therefore show technological advantages in comparison to other polyhydric alcohols. Anhydrous lactitol can be obtained in crystalline form from solutions in absolute ethanol. It melts at 146° C. and is non hygroscopic.

Anhydrous maltitol can be obtained as a crystalline powder from solutions in absolute ethanol after seeding with seed crystals. It melts at 146° to 148° C. and is hygroscopic (Helv. Chem. Acta 20, (1937), 86° to 90). All of the sugar alcohols prepared according to the invention have a content of catalyst constituents of below 3 ppm; they are generally epimer-free.

"Epimer-free" in the context of the present invention is taken to mean a content of epimers which is negligible for the purity of the said sugar alcohols to the extent that these sugar alcohols comply with the commercial specifications as given in the German Pharmacopeia (DAB) and in the United States Pharmacopeia (USP) and in the Food Chemicals Codex (FCC) without further purification operations.

The sugar alcohols are obtained in the process according to the invention in a virtually quantitative yield. This is of particular importance, since the removal of interferring higher-molecular (resulting from ether formation) or lower-molecular (resulting from hydrogenolysis) impurities from the reaction product by additional purification processes such as recrystallization from solvents generally requires a considerable ecological expenditure with respect to their disposal. The sugar alcohol xylitol epimers of the lyxitol type (or of arabitol and ribitol) can be detected in the reaction product at most in traces (total<0.3% by weight). The sorbitol epimer mannitol is present in the reaction product at most in traces (<0.3% by weight). The lactitol diastereomer 4-O-β-D-galactopyranosyl-D-mannitol and the maltitol diastereomer 4-O-α-D-glucopyranosyl-D-mannitol are not detectable in the respective reaction product.

The oxygen-free and support-free fixed-bed catalysts to be used according to the invention, in contrast to support-containing catalysts, do not have a tendency to "bleed", i.e. do not have a tendency to transfer catalyst constituents in ionic or colloidal form into the solution phase of the substrate so that the substrate does not become contaminated by heavy metals which likewise can usually only be removed from the substrate with difficulty, for example with the aid of ion exchangers. The catalyst metals to be used can easily be processed and reused after their use since the heavy metals do not have to be separated laboriously from a support material. In the case of polyhydroxyl compounds, there was furthermore the risk of a tendency to form complex chelate compounds with heavy metal ions, which chelate compounds can only be removed with difficulty from the sugar alcohol solutions.

The sweetening power of xylitol attains about 80 to 100% of the sweetening power of sucrose.

Because of its pleasant taste, xylitol is suitable as a sugar substitute in the diet of diabetics and as a non cariogenic sweetener in confectionary products and oral pharmaceuticals. Xylitol is permitted without restriction on quantity for diabetic foods by the German Dietetic Foods Ordinance (Bundesgesetzblatt 1, 1982, page 71).

Xylitol is particularly suitable for the processing of confectionery products such as sweets and chewing gum (Swiss Dent. 1, (⅞) 1980, pages 25 to 27). Products for treating the oral and pharyngial cavity such as toothpastes, antiseptic throat tablets and cough sweets are also increasingly being sweetened with xylitol (Swiss Dent. III, (⅞) 1982, pages 25 to 30).

The sweetening power of sorbitol attains about 50 to 60% of the sweetening power of sucrose. To increase the sweetening power, artificial sweeteners, for example cyclohexylsulphamate or aspartylphenylalanine methyl ester, can be added to the aqueous solution and the mixture can be obtained in crystalline form by joint vacuum crystallization. However, the artificial sweeteners can also be mixed with the sorbitol crystals in solid form. Sorbitol can also be mixed in liquid or solid form with other sweet-tasting sugar alcohols, for example xylitol, maltitol, lactitol and others.

Sorbitol is absorbed in the human body only in a minor amount and only this portion is metabolized. Sorbitol is therefore suitable as a sugar substitute for diabetics and as a low-calorie sweetener. In addition, it is less cariogenic than sucrose or other sugars.

Lactitol is not metabolized as a carbohydrate in the human body and is neither hydrolyzed nor absorbed in the small intestine. Lactitol is therefore suitable as a sugar substitute for diabetics. In addition it is less cariogenic than sucrose.

The sweetening power of lactitol attains about 40% of the sweetening power of sucrose. To increase the sweetening power, as in the case of sorbitol, artificial sweeteners can be added to the aqueous solution and the mixture can be obtained in crystalline form by joint vacuum crystallization. However, the artificial sweeteners can also be mixed in solid form with the lactitol crystals. In addition, lactitol can be mixed in liquid or solid form with other sweet-tasting sugar alcohols, for example sorbitol, xylitol and others.

Toxic effects of xylitol, sorbitol and lactitol could not be detected even in long-term studies (Ullmanns Encyclop ädie der technischen Chemie, [Ullmanns Encyclopaedia of Industrial Chemistry], Volume 24, Weinheim 1983, p. 779), so that versatile applications result in the food sector, in the production of diabetic products and of sugar-free confectionery products and foods with low nutritive value.

Maltitol is broken down only with difficulty in the human body by amylolytic enzymes. Maltitol is therefore suitable as a sugar substitute for a reduced-calorie diet and for diabetics (Ullmanns Encyclopädie der technischen Chemie [Ullmanns Encyclopaedia of Industrial Chemistry], Volume 24, Weinheim 1983, p. 771).

The sweetening power of maltitol attains the sweetening power of sucrose. Maltitol can be mixed in liquid form with other sweet-tasting sugar alcohols, for example sorbitol, xylitol and others. Use particularly in the beverage industry is recommended because of its high sweetening power and its low tendency to crystallization even at high concentrations.

The percentages of the following examples are each by weight.

EXAMPLES

Example 1

A vertically upright, heat-insulated high-pressure tube made of stainless steel of 45 mm internal diameter and 1 m in length was packed with 1.4 l of a hydrogenation catalyst prepared by tableting a metal powder of an Ni/Mo alloy having an Mo content of 1.74%, which hydrogenation catalyst at a cylinder height of 5 mm and a diameter of 5 mm had a compressive strength of 191 N on the lateral cylinder surface and an internal surface area of 58 m$^2$/g. Through this tube was continuously pumped 250 ml hourly of a 40% strength solution of D-xylose in deionized oxygen-free drinking water having a pH of 7.0 together with the threefold molar amount of highly pure hydrogen at a pressure of 300 bar, more precisely rising from bottom to top.

Aqueous solution and hydrogen were jointly conducted in advance through a heat exchanger and heated to the extent that they entered the high-pressure tube at a temperature of 70° C. The mixture of aqueous solution and excess hydrogen leaving the high-pressure tube was conducted via a cooler into a separator from where the hydrogen, after replacement of the amount used, was pumped back into the preheater together with fresh D-xylose solution and from there again into the high-pressure tube. The colorless and clear aqueous solution was depressurized and concentrated in a falling-film evaporator to a sugar alcohol content of approximately 75% and then brought to crystallization after further evaporation in a vacuum crystallizer with cooling. A white, slightly hygroscopic, odorless solid product was obtained which was processed to give a fine-crystalline powder. The xylitol formed was otherwise highly pure and, in the stable rhombic crystal form, showed a melting point of 93 to 94° C. The content of non-hydrogenated D-xylose was ≦0.2%. Ni and Mo contents were <1 ppm. The catalyst was active without change even after a running time of 2600 hours.

Example 2

Through a high-pressure tube as in Example 1 but made of high-pressure steel N9, the hydrogen was conducted in counter-current to the rising solution of D-xylose in reverse reaction flow to that in Example 1 at a temperature of 65° C. and a hydrogen pressure of 150 bar, where an equal amount of a 40% strength aqueous solution of D-xylose was hydrogenated per hour, which solution had a pH of 7.0. The catalyst had been produced by tableting metal powder of an Ni/Cr alloy having a Cr content of 2.1% which was additionally alloyed with a Ti portion of 4.5%. The tablets, at a cylinder height of 5 mm and a diameter of 5 mm had a compressive strength of 210 N on the lateral cylinder surface and an internal surface area of 71 $m^2/g$. After a running time of 1800 hours with undiminished activity, the conversion rate of D-xylose was $\geq 99.8\%$. The content of non-hydrogenated D-xylose in the crystallized xylitol which had a purity of $\geq 99.5\%$ was 0.2%. Ni and Cr contents were 1 ppm.

Example 3

In a high-pressure tube as in Example 1, an equal amount per hour of a 40% strength aqueous solution of D-xylose which had a pH of 7.5 was hydrogenated in the same manner as in Example 1 at a temperature of 65° C. and a hydrogen pressure of 300 bar. The catalyst had been obtained by tableting an Ni/Fe/Cr alloy. The alloy had an Fe content in Ni of 15% and a Cr content of 4.5%. The tablets, at a cylinder height of 5 mm and a diameter of 5 mm, had a compressive strength of 167 N on the lateral cylinder surface and an internal surface area of 68 $m^2/g$. The crystalline xylitol obtained in a vacuum crystallizer by seeding with seed crystals had a purity of $\geq 99.5\%$. The content of unconverted D-xylose was 0.1%. Ni, Fe and Cr contents were <1 ppm. After a running time of 1200 hours, the activity of the catalyst was still unchanged.

Example 4

In a high-pressure tube as in Example 1, 150 ml per hour of a 40% strength aqueous solution of D-xylose which had a pH of 6.5 were hydrogenated in the same manner as in Example 1 at a temperature of 80° C. and a hydrogen pressure of 300 bar. The catalyst was obtained by tableting a Co/Mo alloy having an Mo content of 3.8%. The tablets, at a cylinder height of 5 mm and a diameter of 5 mm, had a compressive strength of 185 N on the lateral cylinder surface and an internal surface area of 44 $m^2/g$. The xylitol obtained in a vacuum rotary tube had a content of unreacted D-xylose of $\leq 0.2\%$. The Co and Mo contents were <1 ppm. After a running time of 1000 hours, the activity of the catalyst was still undiminished.

Example 5

A high-pressure tube as in Example 1 was packed with 1.4 l of a hydrogenation catalyst prepared by tableting metal powder of an Ni/Mo alloy having an Mo content of 1.75%, which hydrogenation catalyst at a cylinder height of 5 mm and a diameter of 5 mm had a compressive strength of 191 N on the lateral cylinder surface and an internal surface area of 58 $m^2/g$. Through this tube were pumped continuously 250 ml per hour of a 40% strength solution of α-D-glucose in deionized oxygen-free drinking water having a pH of 7.0 together with the threefold molar amount of highly pure hydrogen at a pressure of 200 bar, more precisely ascending from bottom to top. Aqueous solution and hydrogen had previously been jointly conducted through a heat exchanger and heated to the extent that they entered the high-pressure tube at a temperature of 70° C. The mixture of aqueous solution and excess hydrogen leaving the high-pressure tube was conducted via a cooler into a separator from where the hydrogen, after replacement of the amount used, was pumped back into the preheater together with fresh α-D-glucose solution and from there again into the high-pressure tube. The colorless and clear aqueous solution was depressurized and concentrated in a falling-film evaporator to a sugar alcohol content of approximately 70% and then brought to crystallization after further evaporation in a vacuum crystallizer with cooling. A white, slightly hygroscopic, odorless solid product was obtained which was ground to give a finely crystalline powder. The sorbitol formed was otherwise highly pure and in the stable γ form had a melting point of 101° C. The content of non-hydrogenated α-D-glucose was $\leq 0.1\%$. Ni and Mo contents were <1 ppm. Even after a running time of 4200 hours, the activity of the catalyst was unchanged.

Example 6

Through a high-pressure tube as in Example 1, the hydrogen was conducted in counter-current to the ascending solution of α-D-glucose in reverse reaction flow to that described in Example 1 at a temperature of 75° C. and a hydrogen pressure of 300 bar, in which case an amount per hour of 40% strength aqueous solution of α-D-glucose equal to that in Example 1 which had a pH of 7.0 was hydrogenated. The catalyst had been prepared by tableting a metal powder of an Ni/Cr alloy having a Cr content of 2.1% which was alloyed with a Ti content of 4.5%. The tablets, at a cylinder height of 5 mm and a diameter of 5 mm, had a compressive strength of 210 N on the lateral cylinder surface and an internal surface area of 71 $m^2/g$. After a running time of 2200 hours with undiminished activity, the conversion rate of α-D-glucose was 99.9%. The content of non-hydrogenated α-D-glucose in the crystallized sorbitol which had a purity of $\geq 99.5\%$ was $\leq 0.1\%$. The Ni content was <1 ppm. The Cr and Ti contents were 1 ppm.

Example 7

In a high-pressure tube as in Example 1, an equal amount per hour of a 40% strength aqueous solution of α-D-glucose which had a pH of 7.5 was hydrogenated in the same manner as in Example 1 at a temperature of 65° C. and a hydrogen pressure of 300 bar. The catalyst had been obtained by tableting a pulverized Ni/Fe/Cr alloy. The alloy had an Fe content in Ni of 15% and a Cr content of 4.5%. The tablets, at a cylinder height of 5 mm and a diameter of 5 mm, had a compressive strength of 167 N on the lateral cylinder surface and an internal surface area of 68 $m^2/g$. The crystalline sorbitol obtained in a vacuum crystallizer had a purity of $\geq 99.5\%$. The content of unconverted α-D-glucose was 0.2%. Ni, Cr and Fe contents were each <1 ppm. After a running time of 1400 hours, the activity of the catalyst was still unchanged.

Example 8

In a high-pressure tube as in Example 1, 150 ml per hour of a 35% strength aqueous solution of α-D-glucose which had a pH of 7.5 were hydrogenated in the same manner as in Example 1 at a temperature of 70° C. and a hydrogen pressure of 300 bar. The catalyst had been obtained by tableting metal powder of an Ni/Mo alloy having an Mo content of 1.6% which additionally had an Al content of 6.1%. The tablets, at a cylinder height of 5 mm and a diameter of 5 mm, had a compressive strength of 210 N on the lateral cylinder surface and an internal surface area of 71 $m^2/g$. The sorbitol obtained in a vacuum rotary tube had a content of unconverted α-D-glucose of $\leq 0.2\%$. Ni, Al and Mo contents were each 1 ppm. After a running time of 1300 hours, the activity of the catalyst was still undiminished.

Example 9

A high-pressure tube as in Example 1, was packed with 1.4 l of a hydrogenation catalyst prepared by tableting metal powder of an Ni/Fe/Mo alloy having an Fe content of 15% and an Mo content of 1.4%, which hydrogenation catalyst, at a cylinder height of 3 mm and a diameter of 3 mm, had a compressive strength of 162 N on the lateral cylinder surface and an internal surface area of 68 m$^2$/g. Through this tube were continuously pumped 200 ml per hour of a 40% strength solution of 4-O-β-D-galactopyranosyl-α-D-glucopyranose in deionized oxygen-free drinking water having a pH of 7.0 together with the threefold molar amount of highly pure hydrogen at a pressure of 300 bar, more precisely rising from bottom to top. Aqueous solution and hydrogen had been previously conducted together through a heat exchanger and heated to the extent that they entered the high-pressure tube at a temperature of 70° C. The mixture of aqueous solution and excess hydrogen leaving the high-pressure tube was conducted via a cooler into a separator from where the hydrogen, after replacement of the mount used, was pumped back into the preheater together with fresh 4-O-β-D-galactopyranosyl-α-D-glucopyranose and from there again into the high-pressure tube. The colourless and clear aqueous solution was depressurized and concentrated in a falling-film evaporator to a sugar alcohol content of approximately 80% and then brought to crystallization after further evaporation in a vacuum crystallizer with cooling. Depending on the crystallization conditions and the residual water content of the evaporated solution, either the dihydrate having a melting point from 76° to 78° C. or the monohydrate having a melting point from 121° to 123 ° C. could be isolated; the 4-O-β-D-galactopyranosyl-D-sorbitol formed was otherwise pure (purity≧99.6%). The content of non-hydrogenated 4-O-β-D-galactopyranosyl-α-D-glucopyranose was <0.2%. The content of sorbitol was ≦0.1%. 4-O-β-D-Galactopyranosyl-D-mannitol or mannitol could not be detected. Ni content, Fe content and Mo content were 1 ppm. After a running time of 1700 hours, the activity of the catalyst was still unchanged.

Example 10

Through a high-pressure tube as used in Example 1, the hydrogen was conducted in counter-current to the ascending solution of 4-O-β-D-galactopyranosyl-α-D-glucopyranose in reverse reaction flow to that described in Example 1 at a temperature of 65° C. and a hydrogen pressure of 150 bar, in which case an amount per hour of a 40% strength aqueous solution of 4-O-β-D-galactopyranosyl-α-D-glucopyranose equal to that in Example 1 which had a pH of 6.5 was hydrogenated. The catalyst had been prepared by tableting from metal powder of an Ni/Mo/Al alloy having an Mo content of 1.62% and an Al content of 6.1%. The tablets, at a cylinder height of 5 mm and a diameter of 5 mm, had a compressive strength of 210 N on the lateral cylinder surface and an internal surface area of 71 m$^2$/g. After a running time of 1800 hours with undiminished activity, the content of 4-O-β-D-galactopyranosyl-D-sorbitol of the reaction mixture evaporated to dryness in a rotary evaporator was 99.4%. The content of non-hydrogenated 4-O-β-D-galactopyranosyl-α-D-glucopyranose was ≦0.2%. The content of sorbitol was 0.1%. 4-O-β-D-Galactopyranosyl-D-mannitol or mannitol could not be detected. Ni, Mo and Al contents were <3 ppm.

Example 11

In a high-pressure tube as used in Example 1, an equal amount per hour of a 40% strength aqueous solution of 4-O-β-D-galactopyranosyl-α-D-glucopyranose which had a pH of 7.5 was hydrogenated in the same manner as in Example 1 at a temperature of 70° C. a cylinder height of 5 mm and a diameter of 5 mm, had a compressive strength of 210 N Mn alloy. The alloy had a Cr content of 3.8% and an Mn content of 2.4%. The tablets, at a cylinder height of 5 mm and a diameter of 5 mm, had a compressive strength of 195 N on the lateral cylinder surface and an internal surface area of 74 m$^2$/g. The 4-O-β-D-galactopyranosyl-α-D-sorbitol obtained in a vacuum crystallizer had a purity of 99.3%. The content of unconverted 4-O-β-D-galactopyranosyl-α-D-glucopyranose was 0.1%. The sorbitol content was 0.1%. 4-O-β-D-Galactopyranosyl-D-mannitol or mannitol could not be detected. Ni, Cr and Mn contents were <2 ppm. After a running time of 1994 hours, the activity of the catalyst was still unchanged.

Example 12

In a high-pressure tube as used in Example 1, the same amount of a 30% strength aqueous solution of 4-O-β-D-galactopyranosyl-α-D-glucopyranose which had a pH of 6.5 was hydrogenated in the same manner as in Example 1 at a temperature of 65° C. and a hydrogen pressure of 200 bar. The catalyst had an Mo content of 1.61% and an At content of 6.1%. The tablets, at a cylinder height of 5 mm and a diameter of 5 mm, had a compressive strength of 210 N on the lateral cylinder surface and an internal surface area of 71 m$^2$/g. The 4-O-β-D-galactopyranosyl-α-D-sorbitol obtained in a vacuum rotary tube had a purity of 99.4%. The content of unconverted 4-O-β-D-galactopyranosyl-α-D-glucopyranose was 0.2%. The sorbitol content was 0.2%. 4-O-β-D-Galactopyranosyl-D-mannitol or mannitol could not be detected. After a running time of 1900 hours, the activity of the catalyst was still undiminished.

Example 13

A high-pressure tube as in Example 1, was packed with 1.4 l of a hydrogenation catalyst prepared by tableting metal powder of an alloy of Ni/Cr/Ti having a Cr content of 2.1% and a Ti content of 4.5%, which hydrogenation catalyst, at a cylinder height of 5 mm and a diameter of 5 mm, had a compressive strength of 210 N on the lateral cylinder surface and an internal surface area of 71 m$^2$/g. Through this tube were continuously pumped 250 ml per hour of a 40% strength aqueous solution of 4-O-β-D-galactopyranosyl-α-D-glucopyranose in deionized oxygen-free drinking water having a pH of 7.0 together with the fivefold molar mount of highly pure hydrogen at a pressure of 300 bar, more precisely rising from bottom to top. Aqueous solution and hydrogen had been previously conducted together through a heat exchanger and heated to the extent that they entered the high-pressure tube at a temperature of 60° C. The mixture of aqueous solution and excess hydrogen leaving the high-pressure tube was conducted via a cooler into a separator from where the hydrogen, after replacement of the amount used, was pumped back into the preheater together with fresh 4-O-β-D-galactopyranosyl-α-D-glucopyranose and from there again into the high-pressure tube. The colourless and clear aqueous solution was depressurized and concentrated in a falling-film evaporator to a sugar alcohol content of approximately 80% and then brought to crystallization after further evaporation in a vacuum crystallizer with cooling and, if appropriate, addition of seed crystals. The crystalline 4-O-β-D-galactopyranosyl-D-sorbitol had a purity content of ≧99.3%. The content of non-hydrogenated 4-O-J3-D-galactopyranosyl-α-D-glucopyranose was ≦0.2%. The content of sorbitol was ≦0.3%. Mannitol could not be detected. Even after a running time of 2800 hours, the activity of the catalyst was unchanged.

Example 14

Through a high-pressure tube as used in Example 1, the hydrogen was conducted in counter-current to the rising solution of 4-O-β-D-galactopyranosyl-α-D-glucopyranose in reverse reaction flow to that described in Example 1 at a temperature of 70° C. and a hydrogen pressure of 200 bar, in which case an amount per hour of 40% strength aqueous solution of 4-O-β-D-galactaopyranosyl-α-D-glucopyranose equal to that in Example 1 which had a pH of 6.5 was hydrogenated. The catalyst was prepared by tableting Ni/Mo/Al powder having an Mo content of 1.6% and an Al content of 6.1%. The tablets, at a cylinder height of 5 mm and a diameter of 5 mm, had a compressive strength of 210 N on the lateral cylinder surface and an internal surface area of 71 m²/g. After a running time of 1900 hours with undiminished activity, the content of 4-O-β-D-galactopyranosyl-D-sorbitol of the reaction mixture evaporated to dryness in a rotary evaporator was 99.2%. The content of non-hydrogenated 4-O-β-D-galactopyranosyl-α-D-glucopyranose was ≦0.2%. The content of sorbitol was 0.3%.

Example 15

In a high-pressure tube as used in Example 1, an equal amount per hour of a 40% strength aqueous solution of 4-O-β-D-galactopyranosyl-α-D-glucopyranose which had a pH of 7.5 was hydrogenated in the same manner as in Example 1 at a temperature of 60° C. and a hydrogen pressure of 300 bar. The catalyst was prepared by tableting a pulverized Ni/Fe/Cr alloy having an Fe content of 15% and a Cr content of 4.5%. The tablets, at a cylinder height of 5 mm and a diameter of 5 mm, had a compressive strength of 167 N on the lateral cylinder surface and an internal surface area of 68 m²/g. The 4-O-β-D-galactopyranosyl-α-D-sorbitol obtained in a vacuum evaporator had a purity of 99.1%. The content of unconverted 4-O-β-D-galactopyranosyl-α-D-glucopyranose was 0.2%. The sorbitol content was 0.3%. Ni, Fe and Cr contents were <3 ppm. After a running time of 1200 hours, the activity of the catalyst was still unchanged.

Example 16

In a high-pressure tube as used in Example 1, the same amount of a 30% strength aqueous solution of 4-O-β-D-galactopyranosyl-α-D-glucopyranose which had a pH of 6.5 was hydrogenated in the same manner as in Example 1 at a temperature of 65° C. and a hydrogen pressure of 200 bar. The catalyst was obtained by tableting a metal powder of an Ni/Mo/Al alloy having an Mo content of 0.55% and an Al content of 6.5%. The tablets, at a cylinder height of 5 mm and a diameter of 5 mm, had a compressive strength of 197 N on the lateral cylinder surface and an internal surface area of 64 m²/g. The 4-O-β-D-galactopyranosyl-α-D-sorbitol obtained in a vacuum rotary tube had a purity of 99.3%. The content of unconverted 4-O-β-D-galactopyranosyl-α-D-glucopyranose was 0.1%. The sorbitol content was 0.3%. After a running time of 3600 hours, the activity of the catalyst was unchanged.

I claim:

1. A process for the preparation of sugar alcohols selected from the group consisting of xylitol, sorbitol, 4-O-β-D-galactopyranosyl-D-sorbitol and 4-O-α-D-glucopyranosyl-D-sorbitol by catalytic hydrogenation of the corresponding sugars D-xylose, α-D-glucose, 4-O-β-D-galactopyranosyl-α-D-glucopyranose and 4-O-α-D-glucopyranosyl-α-D-glucopyranose in aqueous solution with hydrogen at elevated pressure and elevated temperature, characterized in that the hydrogenation is carried out continuously at a hydrogen pressure of 100 to 400 bar, and temperatures of 40 to 80° C., in the fixed-bed process in a reaction zone over support-free shaped bodies serving as hydrogenation catalysts having a compressive strength of 20 to 250 N, and an internal surface area of 10 to 80 m²/g and comprising an alloy of at least three-metals, at least one of which is selected from the group consisting of iron, cobalt and nickel and at least one of which is selected from the group consisting of Cr, Mo and W.

2. The process according to claim 1, characterized in that the shaped bodies are those composed of pressed metal powders.

3. The process according to claim 1, characterized in that the shaped bodies viewed macroscopically have a smooth surface.

4. The process according to claim 1, characterized in that the shaped bodies are cylindrical or spherical and have diameters from 3 to 7 mm.

5. The process according to claim 1, characterized in that the hydrogenation of the sugars is carded out in 15 to 45% aqueous solution at a pH of 3.5 to 8.5.

6. The process according to claim 1, characterized in that the catalyst comprises an alloy of nickel, molybdenum and aluminum.

7. The process according to claim 1, characterized in that the material being reduced comprises 4-O-β-D-galactopyranosyl-α-D-glucopyranosyl-α-D-glucopyranose.

8. The process of claim 1, wherein said alloy comprises, in addition to said at least one-metal selected from the group consisting of iron, cobalt and nickel, and said at least one-metal selected from the group consisting of chromium, molybdenum and tungsten; one or more metals selected from the group consisting of aluminum, silicon, titanium and manganese, wherein the amount of aluminum, if present, is not more than 10% by weight of alloy and the amount of silicon, titanium or manganese, if present, is not more than 5% by weight of alloy.

9. The process of claim 8, wherein said alloy is an alloy of nickel, iron and molybdenum.

10. The process of claim 8, wherein said alloy is an alloy of nickel, molybdenum and aluminum.

11. The process of claim 8, wherein said alloy is an alloy of nickel, chromium and manganese.

12. The process of claim 8, wherein said alloy is an alloy of nickel, chromium and titanium.

13. The process of claim 8, wherein said alloy is an alloy of nickel, iron and chromium.

* * * * *

UNITED STATES PATENT AND TRADEMARK OFFICE
CERTIFICATE OF CORRECTION

PATENT NO. : 5,641,872
DATED : June 24, 1997
INVENTOR(S) : Darsow, Gerhard

It is certified that error appears in the above-indentified patent and that said Letters Patent is hereby corrected as shown below:

Title Page        ABSTRACT: Line 4 delete " carded " and substitute -- carried --

Col. 14, line 34    Delete " carded " and substitute -- carried --

Signed and Sealed this

Seventeenth Day of March, 1998

Attest:

BRUCE LEHMAN

Attesting Officer    Commissioner of Patents and Trademarks